(12) United States Patent
Cameron et al.

(10) Patent No.: US 8,359,100 B2
(45) Date of Patent: Jan. 22, 2013

(54) METHOD FOR SELECTING ELECTRODES FOR DEEP BRAIN OR CORTICAL STIMULATION AND PULSE GENERATOR FOR DEEP BRAIN OR CORTICAL STIMULATION

(75) Inventors: Tracy L. Cameron, Toronto (CA); Rohan Hoare, Dallas, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 593 days.

(21) Appl. No.: 12/137,365

(22) Filed: Jun. 11, 2008

(65) Prior Publication Data
US 2009/0005833 A1    Jan. 1, 2009

Related U.S. Application Data

(60) Provisional application No. 60/945,193, filed on Jun. 20, 2007.

(51) Int. Cl.
*A61N 1/00* (2006.01)
(52) U.S. Cl. .................. 607/45; 607/42; 607/48
(58) Field of Classification Search ............ 607/42, 607/45, 48
See application file for complete search history.

(56) References Cited

U.S. PATENT DOCUMENTS

| | | | |
|---|---|---|---|
| 5,462,545 A | 10/1995 | Wang et al. | |
| 5,649,970 A | 7/1997 | Loeb et al. | |
| 5,683,422 A | 11/1997 | Rise | |
| 5,792,186 A | 8/1998 | Rise | |
| 6,038,480 A | 3/2000 | Hrdlicka et al. | |
| 6,064,905 A | 5/2000 | Webster, Jr. et al. | |
| 6,473,653 B1 | 10/2002 | Schallhorn et al. | |
| 7,151,961 B1 | 12/2006 | Whitehurst et al. | |
| 7,200,446 B2 | 4/2007 | Borkan | |
| 7,212,867 B2 | 5/2007 | Van Venrooij et al. | |
| 7,668,601 B2 | 2/2010 | Hegland et al. | |
| 7,761,985 B2 | 7/2010 | Hegland et al. | |

(Continued)

FOREIGN PATENT DOCUMENTS

WO   2006041871 A2   4/2006

OTHER PUBLICATIONS

Kendall H. Lee, M.D., et al., "Neurotransmitter release from high-frequency stimulation of the subthalamic nucleus," J. Neurosurg., vol. 101, pp. 511-517, Sep. 2004.

(Continued)

*Primary Examiner* — Nicole F Lavert
(74) *Attorney, Agent, or Firm* — Christopher S. L. Crawford; Craig Hoersten

(57) ABSTRACT

In one embodiment, a system for electrically stimulating neural tissue of a patient and for determining neurotransmitter release in response to stimulation, the system comprises: pulse generating circuitry for generating electrical pulses; at least one electrical lead for conducting electrical pulses generated by the pulse generating circuitry to neural tissue, the at least one electrical lead comprising a plurality of electrodes; at least one electrochemical sensor for sensing an extracellular level of one or several neurotransmitters; circuitry for sampling a signal from the at least one electrochemical sensor; a controller for automatically applying stimulation to neural tissue using a plurality of electrode combinations, the controller generating data related to neurotransmitter release for each of the plurality of electrode combinations; and a display for displaying neurotransmitter release for electrode combinations to a clinician.

8 Claims, 3 Drawing Sheets

U.S. PATENT DOCUMENTS

| | | |
|---|---|---|
| 2002/0013612 A1 | 1/2002 | Whitehurst |
| 2002/0183817 A1 | 12/2002 | Van Venrooij et al. |
| 2003/0120328 A1 | 6/2003 | Jenkins et al. |
| 2005/0060885 A1 | 3/2005 | Johnson et al. |
| 2005/0246004 A1 | 11/2005 | Cameron et al. |
| 2006/0058588 A1 | 3/2006 | Zdeblick |
| 2006/0173262 A1 | 8/2006 | Hegland et al. |
| 2006/0241417 A1 | 10/2006 | Edwardsen et al. |
| 2007/0100389 A1* | 5/2007 | Jaax et al. ..................... 607/42 |
| 2008/0039916 A1 | 2/2008 | Colliou et al. |
| 2008/0114230 A1 | 5/2008 | Addis |
| 2008/0215125 A1 | 9/2008 | Farah et al. |
| 2008/0255647 A1 | 10/2008 | Jensen et al. |

OTHER PUBLICATIONS

Kendall H. Lee, et al., "Effect of High-Frequency Stimulation of the Subthalamic Nucleus on Subthalamic Neurons: An Intracellular Study," Stereotactic and Functional Neurosurgery, vol. 80, pp. 32-36, 2003.

* cited by examiner

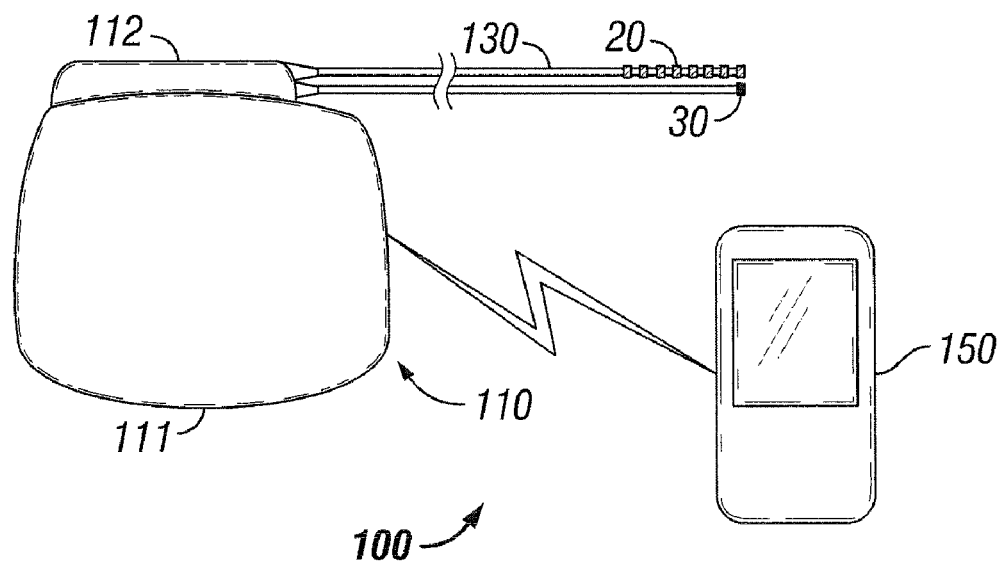
FIG. 1
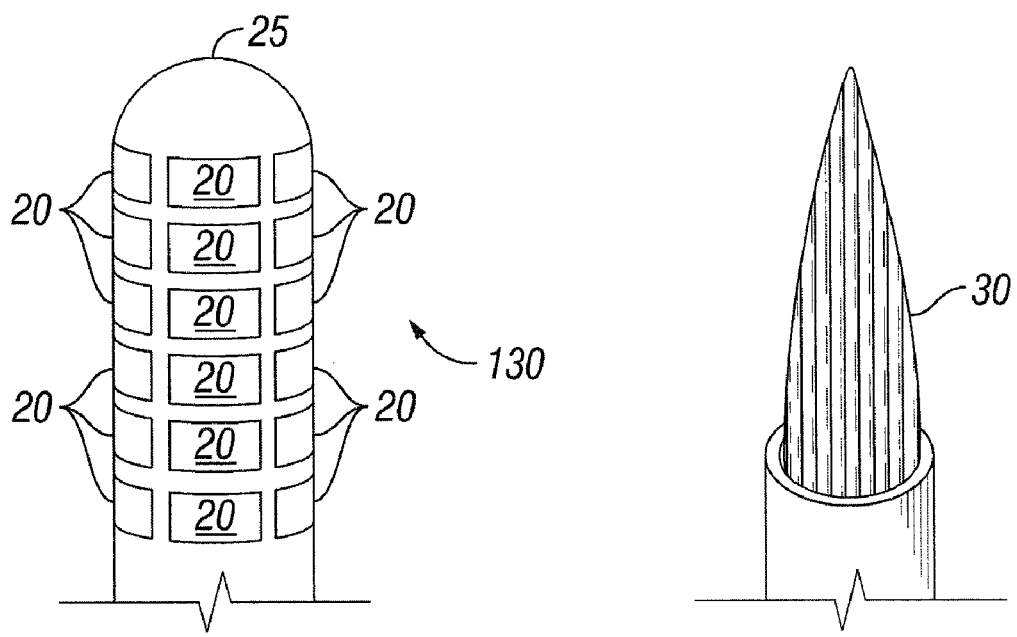
FIG. 2  FIG. 3

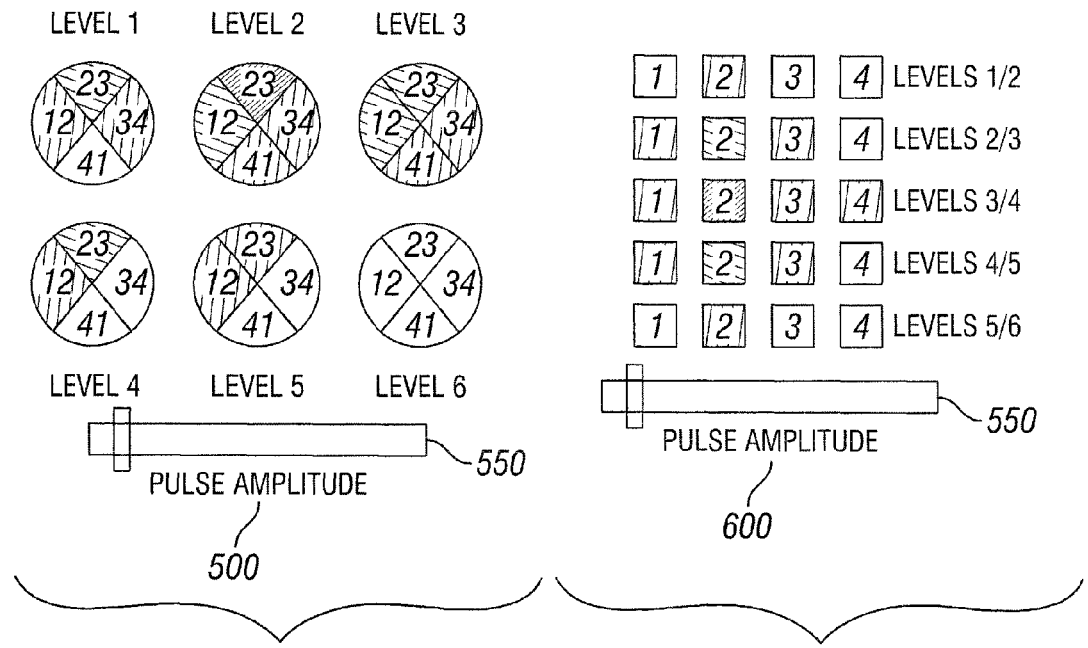
FIG. 5
FIG. 6
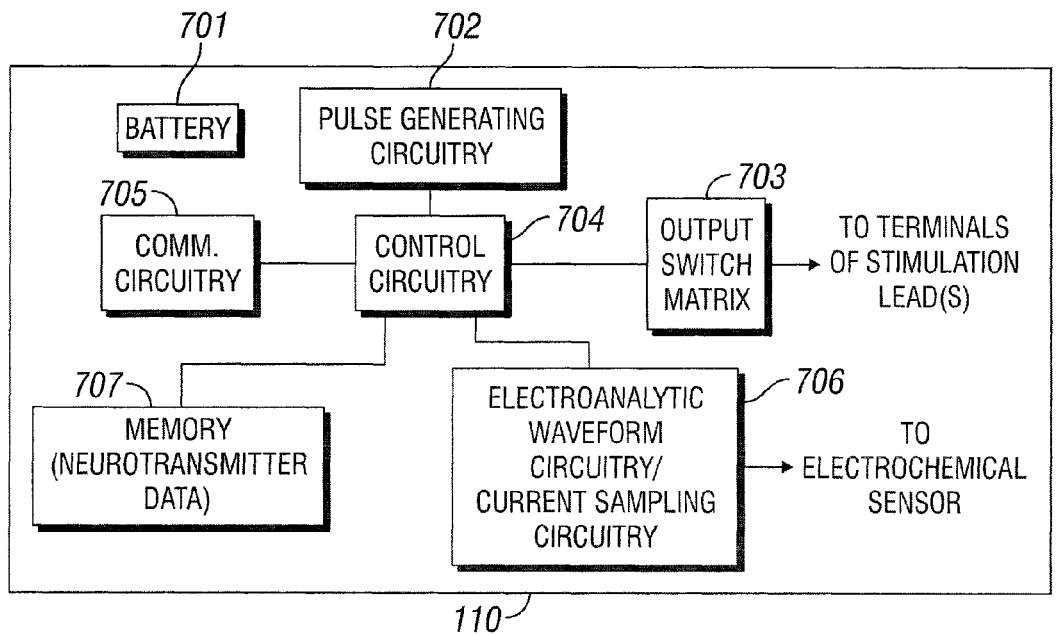
FIG. 7

METHOD FOR SELECTING ELECTRODES FOR DEEP BRAIN OR CORTICAL STIMULATION AND PULSE GENERATOR FOR DEEP BRAIN OR CORTICAL STIMULATION

CROSS-REFERENCE TO RELATED APPLICATIONS

This application claims the benefit of U.S. Provisional Application No. 60/945,193, filed Jun. 20, 2007, the disclosure of which is incorporated herein by reference.

TECHNICAL FIELD

The present application is generally related to selecting one or more electrodes for stimulation of neural tissue within the brain of a patient by mapping neurotransmitter levels in response to stimulation using various electrode combinations.

BACKGROUND

Deep brain stimulation (DBS) refers to the delivery of electrical pulses into one or several specific sites within the brain of a patient to treat various neurological disorders. For example, DBS has been proposed as a clinical technique for treatment of chronic pain, essential tremor, Parkinson's disease (PD), dystonia, epilepsy, depression, obsessive-compulsive disorder, and other disorders.

A DBS procedure typically involves first obtaining preoperative images of the patient's brain (e.g., using computer tomography (CT) or magnetic resonance imaging (MRI)). The imaging process sometimes involves first affixing to the patient's skull fiducial markers that are discernable on the images produced by the imaging process. The fiducial markers assist in registering the preoperative images to the actual physical position of the patient in the operating room during the subsequent surgical procedure. Using the preoperative images, the neurosurgeon can select a target region within the brain, an entry point on the patient's skull, and a desired trajectory between the entry point and the target region. The entry point and trajectory are carefully selected to avoid intersecting or otherwise damaging critical brain structures.

In the operating room, the patient is immobilized and the patient's actual physical position is registered. The physician marks the entry point on the patient's skull and drills a burr hole at that location. A mechanism is provided to precisely control the path through the patient's brain to the desired location. Specifically, a positioning error on the order of a millimeter can have a significant negative effect on the efficacy of the DBS therapy. Stereotactic instrumentation and trajectory guide devices are commercially available products that facilitate the control of the trajectory and positioning of a lead during the surgical procedure.

A microdrive introducer can be used to insert a deep brain stimulation lead toward the selected region of the brain along the selected trajectory. The lead provides one or several conductive paths to deliver stimulation pulses to the selected region. The lead includes a very small diameter insulative lead body with one or several conductors (e.g., stranded wires) embedded in the insulative material. The lead also includes one or several electrodes at a distal end of the lead that are electrically coupled to respective conductors. The electrodes can be used to record signals within the brain and/or to deliver electrical stimulation pulses to brain tissue. Often, the electrical activity adjacent to one or several electrodes is analyzed to determine whether the recorded signals are consistent with the targeted region of the brain. If the recorded signals are not consistent with the targeted region, an adjustment to the lead's position can be made as appropriate.

After the correct location for the stimulation is established, trial stimulation may be provided. The purpose of trial stimulation is to determine whether the stimulation therapy may be effective for the patient's disorder and/or to determine appropriate stimulation parameters for the therapy. If suitable stimulation parameters are identified which are believed to permit treatment of the patient's disorder, an implantable pulse generator is implanted within the patient and the stimulation leads are tunneled to the implanted pulse generator.

One important stimulation parameter is the electrode combination used to apply stimulation to the neural tissue. Specifically, as electrodes are longitudinally distributed along a stimulation lead, selection of different electrodes to apply the electrical pulses changes the specific neural tissue being stimulation. Accordingly, the selection of different electrodes affects the quality of the therapy both in terms of benefits and adverse effects produced by the stimulation.

However, it is not always immediately evident during trial stimulation which electrode combination and other stimulation parameters are optimal. For example, refinement of stimulation parameters for depression may require a significant period of time before suitable stimulation parameters are identified. Specifically, the effectiveness of any single set of parameters is evaluated by monitoring the psychological state of the patient over a time and, hence, each revision of the parameters extends the evaluation process.

BRIEF SUMMARY

In one embodiment, a system for electrically stimulating neural tissue of a patient and for determining neurotransmitter levels in response to stimulation, the system comprises: pulse generating circuitry for generating electrical pulses; at least one electrical lead for conducting electrical pulses generated by the pulse generating circuitry to neural tissue, the at least one electrical lead comprising a plurality of electrodes; at least one electrochemical sensor for sensing levels of one or several neurotransmitters; circuitry for sampling a signal from the at least one electrochemical sensor; a controller for automatically applying stimulation to neural tissue using a plurality of electrode combinations, the controller generating data related to neurotransmitter release for each of the plurality of electrode combinations; and a display for displaying neurotransmitter release for electrode combinations to a clinician.

In another embodiment provides for a method of optimizing electrode selection comprising: implanting at least one electrical lead for conducting electrical pulses generated by a pulse generating circuitry to a first neural tissue, the at least one electrical lead comprising a plurality of electrodes; implanting at least one electrochemical sensor for sensing a level of one or several neurotransmitters in a second neural tissue; applying stimulation to the first neural tissue using a plurality of electrode combinations, sensing the level of one or several neurotransmitters in the second neural tissue using the at least one electrochemical sensor for each of the plurality of electrode combinations; and selecting the electrode or combination of electrodes that provide a desired neurotransmitter level.

Still further, another embodiment provides for a method of optimizing stimulation parameters comprising: implanting at least one electrical lead for conducting electrical pulses generated by a pulse generating circuitry to a first neural tissue, the at least one electrical lead comprising a plurality of electrodes; implanting at least one electrochemical sensor for sensing a level of one or several neurotransmitters in neural tissue; applying stimulation to the neural tissue using a plurality of stimulation parameters, sensing the level of one or several neurotransmitters in a second neural tissue using the at least one electrochemical sensor for each of the plurality of stimulation parameters; and selecting the stimulation parameters that provide a desired neurotransmitter level.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

BRIEF DESCRIPTION OF THE SEVERAL VIEWS OF THE DRAWING

FIG. 1 depicts a stimulation system according to one representative embodiment.

FIG. 2 depicts a stimulation lead having directional electrodes that may be used for one representative embodiment.

FIG. 3 depicts a carbon fiber tip of an electrochemical sensor that may be used for one representative embodiment.

FIG. 5 depicts a display, that may be provided on a programming device, depicting neurotransmitter levels that occurred in response to stimulation using different electrode combinations according to one representative embodiment.

FIG. 6 depicts another display, that may be provided on a programming device, depicting neurotransmitter levels that occurred in response to stimulation using different electrode combinations according to one representative embodiment.

FIG. 7 depicts a pulse generator according to one representative embodiment.

DETAILED DESCRIPTION

Figure 4:
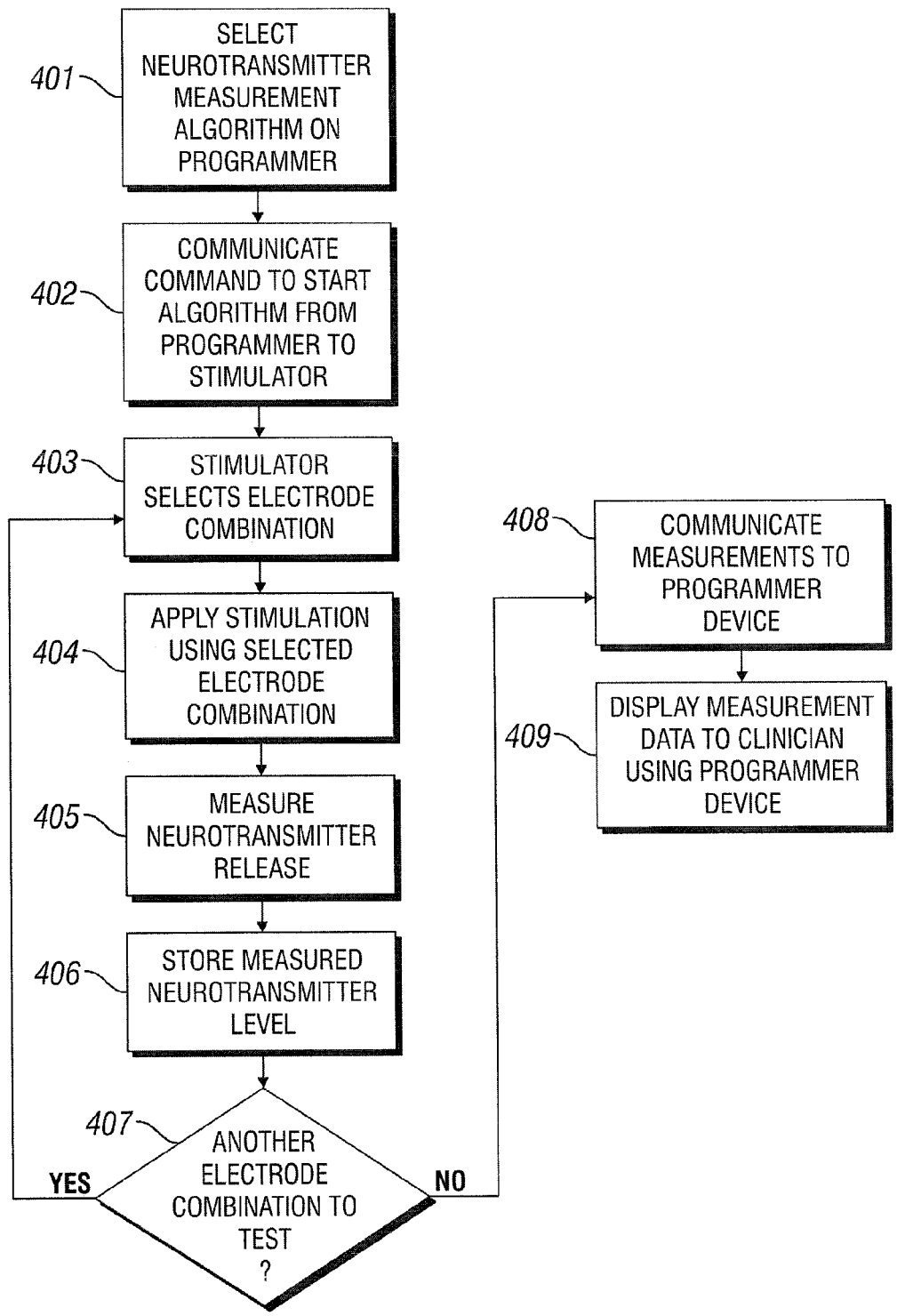
FIG. 4 depicts a flowchart according to one representative embodiment.

FIG. 1 depicts stimulation system 100 for stimulating neural tissue of a patient and automatically measuring neurotransmitter levels according to one representative embodiment. Stimulation system 100 comprises pulse generator 110 which is electrically coupled (possibly through extension leads) to stimulation lead 130 and electrochemical sensor 30. Pulse generator 110 could be an external pulse generator adapted for interoperative or trial stimulation. Alternatively, pulse generator 110 could be an implantable pulse generator. Although one embodiment employs a pulse generator to perform a number of operations, alternative embodiments may employ physically separate devices. For example, a conventional test stimulator system could be employed to provide trial stimulation using a plurality of electrode combinations, a separate electroanalytical system could be employed to measure neurotransmitter levels, and a separate computer system could be employed to associate the recorded neurotransmitter data with the various electrode combinations. Pulse generator 110 comprises metallic housing 111 that encloses the pulse generating circuitry, sensing circuitry, control circuitry, communication circuitry, battery, etc. of the device. An example of pulse generating circuitry is described in U.S. Patent Publication No. 20060170486 entitled "PULSE GENERATOR HAVING AN EFFICIENT FRACTIONAL VOLTAGE CONVERTER AND METHOD OF USE," which is incorporated herein by reference. A microprocessor and associated charge control circuitry for an implantable pulse generator is described in U.S. Pat. No. 7,571,007, entitled "SYSTEMS AND METHODS FOR USE IN PULSE GENERATION," which is incorporated herein by reference. Circuitry for recharging a rechargeable battery of an implantable pulse generator using inductive coupling with an external charging device is described in U.S. Pat. No. 7,212,110, entitled "IMPLANTABLE DEVICE AND SYSTEM FOR WIRELESS COMMUNICATION," which is incorporated herein by reference. In addition, pulse generator 110 is preferably implemented, upon command, to automatically measure neurotransmitter release in response to application of stimulation pulses using a number of electrode combinations.

Stimulation leads are typically connected to a pulse generator through a "header" that contains various connector structures. Connector structures for implantable pulse generators are available from Bal-Seal, Inc. of Foothill, Calif. As shown in FIG. 1, header 112 electrically couples stimulation lead 130 and electrochemical sensor 30 to circuitry within pulse generator 110. Header 112 can be adapted to couple to any suitable number of stimulation leads and/or electrochemical sensor devices. The connector structures (not shown) of header 112 are contained within a suitable housing of epoxy and/or various polymers. The connector structures mechanically and electrically couple to the terminals of the stimulation lead(s) or sensor devices. Also, the connector structures are electrically connected to feedthrough wires. The feedthrough wires extend into the hermetically sealed metallic housing that contains the pulse generating circuitry and sensing circuitry. The term "header" is used in the art, because the header is usually disposed on an upper surface of the metallic housing (although the header can be disposed anywhere on the device as long as it is reasonably accessible).

In a preferred embodiment, stimulation lead 130 is adapted to apply stimulation pulses in a directional manner, rather than uniformly about its circumference. FIG. 2 depicts lead 130 that may be employed according to one representative embodiment. As shown in FIG. 2, lead 130 comprises a plurality of electrodes 20 along the length of lead 130. Additionally, the electrodes 20 of stimulation lead 130 are segmented about the circumference of lead body 25. In one preferred embodiment, four electrodes 20 are fabricated about the circumference of lead body 25 at any given longitudinal position along lead body 25, although any suitable number of electrodes could be so fabricated. By fabricating electrodes 20 in this manner, electrical pulses can be directed to a specific quadrant of neural tissue relative to stimulation lead 130 thereby targeting appropriate neural tissue while avoiding other neural tissue. Electrodes 20 can be fabricated using any suitable biocompatible, biostable material such as platinum or platinum iridium materials. As another example, intrinsically conductive polymers may be employed to fabricate electrodes 20.

In certain embodiments, target neural tissue for use with a DBS device can include subgenual cingulate area, hypothalamus, orbital frontal cortex, anterior insula, medial frontal cortex, dorsolateral prefrontal, dorsal anterior cortex, posterior cingulate area, premotor, orbital frontal, parietal region, ventrolateral prefrontal, dorsal cingulate, dorsal anterior cingulate, caudate nucleus, anterior thalamus, nucleus accumbens, frontal pole, periaqueductal gray area, thalamus, subthalamus, basal ganglia, hippocampus, amygdala, hypothalamus, mammilary bodies, substantia nigra, or caudate putamen.

It shall be appreciated that the use of multiple electrodes 20 along the circumference of stimulation lead 130 significantly increases the number of electrodes 20 relative to conventional stimulation leads. Furthermore, the number of possible electrode combinations for a directional stimulation lead is factorially increased relative to conventional stimulation leads. Determining a suitable electrode combination from the factorially increased number of combinations using conventional manual trial and error programming methods may require an impractical amount of time. Specifically, interoperative trial stimulation may unduly increase the amount of time required by deep brain procedures which are already quite time consuming. Moreover, the ability of a patient to provide feedback regarding the effects of trial stimulation decreases significantly with the length of time of the trial stimulation. Accordingly, some representative embodiments enable appropriate electrode combinations to be selected in a more efficient manner. Additionally, in some cases, electrode combinations and other stimulation parameters may be selected without requiring the patient to be conscious during a deep brain electrode implantation procedure.

Lead body 25 is preferably fabricated using a suitable insulative material. The insulative material of lead body 25 encloses, embeds, or encapsulates the wire conductors (not shown) that conduct electrical pulses between the electrodes and terminals of the lead. Lead body 25 can be fabricated using any conventional or known fabrication technique or any later developed technique. An example of a suitable fabrication technique for forming a lead body 25 with embedded wire conductors can be found in U.S. Pat. No. 7,149,585 which is incorporated herein by reference.

Neurotransmitter sensor 30 is utilized to detect the level of neurotransmitters within an appropriate location within the brain. The level of neurotransmitters detected may be an extracellular level of neurotransmitters, or a cellular level of neurotransmitters or a combination of both extracellular and cellular levels of neurotransmitters. In preferred embodiments, neurotransmitter sensor 30 is utilized to detect an extracellular level of neurotransmitters. Neurotransmitter sensor 30 may be adapted for temporary implantation (e.g., only during the initial DBS procedure). Alternatively, sensor 30 may be adapted for longer term implantation. As shown in FIG. 1, neurotransmitter sensor 30 is implemented separately from stimulation lead 130. When implemented separately, neurotransmitter sensor 30 can be used to measure neurotransmitter levels in a separate region within the brain from the region being stimulated. For example, in PD, it may be desired to electrically stimulate the subthalamic nucleus (STN) and measure dopamine and/or dopamine metabolite levels in the caudate-putamen or substantia nigra. Alternatively, neurotransmitter sensor 30 could be integrated on stimulation lead. Also, multiple sensors 30 could be employed. Multiple sensors 30 could also be disposed immediately adjacent to or interleaved with stimulation electrodes 20. With the use of multiple sensors, multiple neurotransmitters may be measured. For example, in depression, serotonin, norepinephrine, dopamine, and/or γ-amino-butyric (GABA) may be measured to provide the clinician with the appropriate data to achieve the most effective treatment protocol.

Neurotransmitter sensor 30 can be implemented using suitable carbon fiber material. FIG. 3 depicts carbon fiber tip 30 of an electrochemical sensor that can be used to measure neurotransmitter levels for some representative embodiments. The diameter (away from the tip) of the carbon fiber portion of the sensor can be about 5-30 μm. The conductivity, non-toxicity, and small size of carbon fiber microelectrodes enable the electrochemical detection of oxidizable compounds to occur. In particular, catecholamines (epinephrine, norepinephrine, and dopamine) and indolamines (serotonin and melatonin) are accurately measurable using carbon fiber microelectrodes using amperometric detection and differential pulse voltammetry. In particular, the carbon fiber electrodes enable an oxidation current to be measured when the released neurotransmitter is subjected to an applied voltage or current. Other neurotransmitters such as glutamate and acetylcholine can be measured in a similar manner using enzyme modified carbon electrodes. Also, sensitivity to a specific neurotransmitter may be increased using an electrochemical pretreatment of the carbon-fiber to modify its surface chemistry. The agent specific enzyme (for example, glutamate oxidase) or pretreatment is immobilized on the surface of an electrode and the by-product of an oxidation reaction is detected as an applied potential versus a reference electrode. Although carbon fiber sensors have been described, any suitable electrochemical sensor (now existing or later developed) can be utilized according to some representative embodiments. For the purpose of the present application, the term "neurotransmitter" is used in a broad sense and includes, but are not limited to dopamine, acetylcholine, γ-amino-butyric (GABA), aspartate, histamine, adenosine, melatonin, nitric oxide, glycine, glutamate, norepinephrine, epinephrine, serotonin, and their precursors and metabolites (e.g., glutamic acid, aspartic acid, L-DOPA DOPAC, MAO, COMT, etc.). Another class of neurotransmitters that can also be measured according to the methods described herein include neuropeptides, for example, vasopressin, neuropeptide Y, cholecystokinin CCK), Substance P, Substance K, peptide YY, neurotensin, etc.

Referring again to FIG. 1, pulse generator 110 preferably wirelessly communicates with programmer device 150. Programmer device 150 enables a clinician to control the pulse generating operations of pulse generator 110. The clinician can select electrode combinations, pulse amplitude, pulse width, frequency parameters, and/or the like using the user interface of programmer device 150. The parameters can be defined in terms of "stim sets," "stimulation programs," (which are known in the art) or any other suitable format. Programmer device 150 responds by communicating the parameters to pulse generator 110 and pulse generator 110 modifies its operations to generate stimulation pulses according to the communicated parameters.

In some representative embodiments, the clinician can select an option on programmer device 150 to cause pulse generator 110 to execute an algorithm to assist in determining the appropriate stimulation parameters for the patient's specific disorder. Specifically, when directed to begin the algorithm, pulse generator 110 stimulates neural tissue using a number of different electrode combinations and measures neurotransmitter release in response thereto. When pulse generator 110 completes the stimulation and measurements for a number of electrode combinations, pulse generator 110 communicates the measured neurotransmitter levels to programmer device 150. Programmer device 150 then presents the neurotransmitter level data to the clinician in a suitable manner. Using the data, the clinician can attempt to "fine tune" the stimulation parameters. Also, when the clinician adjusts the stimulation parameters using programmer device 150, the neurotransmitter levels may be measured and reported to programmer device 150 to permit the clinician to appreciate the effectiveness of a given set of stimulation parameters.

FIG. 4 depicts a flowchart for automatically measuring neurotransmitter levels to facilitate selection of stimulation parameters according to one representative embodiment. In 401, a clinician selects an icon or other control on a programmer device to execute a neurotransmitter measurement algorithm. In 402, the programmer communicates a command to start the algorithm to the stimulator or pulse generator.

In 403, the stimulator selects an electrode combination. In 404, the stimulator applies stimulation to neural tissue of the patient using the selected electrode combination. In 405, the stimulator measures neurotransmitter release in response to the stimulation. The measurement may occur over any suitable period of time. Also, the period of time may vary depending upon the particular disorder of the patient to be treated using the electrical stimulation. For example, it may be desired to measure serotonin over a longer period of time for depression as compared to the amount of time used to measure dopamine for PD. A number of measurements of the period of time may occur.

In some alternative embodiments, the stimulator may also vary the stimulation amplitude, the stimulation pulse width, the stimulation frequency, or other stimulation characteristic and measure the neurotransmitter effect in response thereto.

In 406, the measurements of the neurotransmitter level(s) are stored in the programmer.

In 407, a logical comparison is made by stimulator to determine whether there is another electrode combination to be tested. In some embodiments, only adjacent electrode pairs are selected for the measurement algorithm. That is, each anode/cathode combination is tested where the anode and cathodes are immediately adjacent to each other (either along the circumference of the stimulation lead and/or along the longitudinal direction of the stimulation lead). By limiting the measurements to adjacent electrodes, the complexity of the algorithm is reduced. However, by providing information pertaining to adjacent electrodes to a clinician, the clinician is provided with sufficient information to enable the clinician to identify the most promising regions of neural tissue for further trial stimulation. If the logical comparison determines that there is a remaining electrode combination to be tested, the process flow returns to 403. If not, the process flow proceeds to 408.

In 408, the stimulator communicates the measurements to the programmer device. The communicated measurement data may include multiple measurements per electrode combination. Alternatively, a single value representing the average neurotransmitter level over the measurement period can be communicated per electrode combination. In 409, neurotransmitter level data is displayed to the clinician using the display of the programmer device.

The measurement data can be presented to the clinician in any suitable format. In a preferred embodiment, the measurement data is present in a graphical format that arranges the data according to the electrode pattern on the stimulation lead. FIGS. 5 and 6 depicts example displays of measurement data according to one representative embodiment.

Display 500 represents the neurotransmitter levels between certain adjacent electrodes on a given circumferential level of a stimulation lead. Each disc graphical element represents a particular circumferential level. Within each disc, each segment represents a particular cathode/anode combination on that level. For example, the segment "1/2" represents the neurotransmitter level that was measured when stimulation pulses were applied with electrode "1" on the given stimulation level operated as a cathode and electrode "2" on the same stimulation level operated as an anode, and all other electrodes operated at a high impedance state. The neurotransmitter level can be graphically represented by the color or shade within the particular disc. In an alternative embodiment, the measured value can be displayed for review by the clinician.

In the particular example of FIG. 5, the clinician can readily appreciate that stimulation at electrode level 2 using electrode "2" as a cathode and using electrode "3" as an anode generated the greatest amount of neurotransmitter release. The clinician can then initiate trial of stimulation parameters around this electrode combination in an effort to identify the stimulation parameters that generate the greatest therapeutic result balancing against adverse effects.

FIG. 6 depicts measurement data displayed in another format. Display 600 displays measurement data for electrodes are adjacent to each other and within the same longitudinal set of electrodes along the stimulation lead. For example, the first box ("1") in "LEVELS 1/2" represents the neurotransmitter level measured when the 1st electrode in the first circumferential level was operated as a cathode, the 1st electrode in the second circumferential level was operated as an anode, and all other electrodes were set to a high impedance state. In a similar manner as display 500, the clinician can visually inspect display 600 to identify a region associated with a highest amount of neurotransmitter release in response to electrical stimulation.

In some embodiments, the clinician may view the neurotransmitter measurements as a function of one or several stimulation parameters such as pulse amplitude, pulse width, pulse frequency, and/or the like. In displays 500 and 600, the clinician may operate amplitude "slide-bar" 550. In response, programmer device 150 may alter the display of the measurement data. Specifically, the color and/or shade of each segment within display 500 or 600 is updated to reflect the neurotransmitter level for the particular cathode/anode combination at the pulse characteristic selected by the clinician. By providing such data, the clinician may be aware of a stimulation threshold beyond which more beneficial therapeutic results are not likely to be obtained. For example, at a certain point, an incremental amount of additional neurotransmitter level may not be worth the adverse effect that is likely from an additional increase in amplitude.

FIG. 7 depicts a block diagram of pulse generator 110 that is adapted to deliver electrical stimulation and measure neurotransmitter levels in accordance with one representative embodiment. Pulse generator 110 comprises battery 701, pulse generating circuitry 702, output switch matrix 703, control circuitry 704, communication circuitry 705, electroanalytic waveform circuitry/current sampling circuitry 706, and memory 707. In one representative embodiment, control circuitry 704 is implemented using a microprocessor and suitable software instructions to implement the appropriate system control. Alternatively, control circuitry 704 may comprise an application specific integrated circuit.

Control circuitry 704 controls the generation of pulses by pulse generating circuitry 702 and the delivery of the generated pulses by output switch matrix 703. Specifically, control circuitry 704 controls the amplitude and pulse width of a respective pulse by controlling pulse generating circuitry 702. Additionally, control circuitry 704 controls the timing or frequency of the generation of pulses by controlling pulse generating circuitry 702. Control circuitry 704 further configures output switch matrix 703 to control the polarity associated with a plurality of outputs associated with switch matrix 703.

Control circuitry 704 further controls electroanalytic waveform circuitry/current sampling circuitry 706 to apply a suitable waveform to the electrochemical sensor and to measure the response to the waveform. Circuitry 706 may comprise suitable driving circuitry, e.g., to apply a fast-scan cyclic voltammetry waveform to sensor 30. Further details regarding fast-scan cyclic voltammetry can be obtained from the article "Detecting Subsecond Dopamine Release with Fast-Scan Voltammetry in vivo," by Robinson et al., Clinical Chemistry, 49: pp. 1763-1773 (2003), which is incorporated herein by reference. Although fast-scan cyclic voltammetry is discussed for this embodiment, any suitable electrochemical detection circuitry could be employed for other embodiments. As is known in the art, in fast-scan cyclic voltammetry, a triangle waveform (potential) is ramped versus a reference (e.g., from 0.4V to +1.0V). The oxidation current in response to the waveform is sampled by circuitry 706. The sampling circuitry may include a suitable amplifier, analog-to-digital converter, etc. The digital samples are communicated from circuitry 706 to control circuitry 704.

In one preferred embodiment, pulse generator 110 (shown in FIG. 1) receives a command from programmer device 150 using communication circuitry 605 to begin automatically applying stimulation pulses to neural tissue and recording the neurotransmitter release that occurs in response to the stimulation pulses. Control circuitry 704 processes the wireless data and responds to the command in the wireless data to begin automatic application of stimulation pulses. The command may identify the neurotransmitter to be measured and control circuitry 704 will control circuitry 706 in response to the identified neurotransmitter.

In fast scan cyclic voltammetry, the digital samples are related to the background current, the oxidation current associated with a neurotransmitter, and current associated with reduction of an electroformed compound back to the neurotransmitter. Control circuitry 704 processes the digital samples to eliminate the background current. Specifically, the background current is typically stable over several seconds and, hence, can be determined by sampling the current (at zero potential) before initiating a given scan. Also, before stimulation pulses are applied for a given electrode combination, the concentration of the respective neurotransmitter is determined to provide a reference value for comparison when stimulation pulses are applied. The concentration the neurotransmitter is related to the current at a specific potential at which the oxidation of that neurotransmitter peaks. Control circuitry 704 compares the current at the appropriate potential to obtain a value that is related to the concentration of the neurotransmitter of interest.

Control circuitry 704 proceeds through a plurality of electrode combinations (and, alternatively, through a plurality of stimulation parameters per electrode combination). Control circuitry 704 processes the digital samples to eliminate the background current and determines the processed value at the oxidation peak of the appropriate neurotransmitter. The processed value is compared against the reference value to determine a change in neurotransmitter concentration that occurred in response to the stimulation. Control circuitry 704 preferably stores the change in neurotransmitter concentration in memory 707. At any suitable point, control circuitry 704 communicates the data in memory 707 to programmer device 150 using communication circuitry 705.

In alternative embodiments, the control and processing operations can be performed by programmer device 150. For example, programmer device 150 may send commands to pulse generator 700 to apply stimulation pulses using specific electrode combinations. Also, programmer device 150 may send commands to pulse generator 700 to measure current associated with sensor 30 at appropriate times. Programmer device 150 may then obtain raw measurement data from pulse generator 700 and perform the appropriate processing to identify neurotransmitter levels.

Although some embodiments have been described in terms of deep brain stimulation, alternative embodiments may apply electrical stimulation to other brain regions. For example, an alternative embodiment may employ cortical stimulation where the stimulation electrodes are positioned extradurally or within the dura directly on the cerebral cortex. In another alternative embodiment, the stimulation lead may be placed extradurally or within the dura of spinal tissue that can include the ascending and descending tracts of the spinal cord. For example, the spinal tissue can include neuronal tissue associated with any of the cervical vertebral segments (C1, C2, C3, C4, C5, C6, C7 and C8) and/or any tissue associated with any of the thoracic vertebral segments (T1, T2, T3, T4, T5, T6, T7, T8, T9, T10, T11, T12) and/or any tissue associated with any of the lumbar vertebral segments (L1, L2, L3, L4. L5, L6) and/or any tissue associated with the sacral vertebral segments (S1, S2, S3, S4, S5). Yet further, in another alternative embodiment, the stimulation lead may be placed subcutaneously adjacent to various peripheral neural tissue (e.g., olfactory nerve, optic, nerve, oculomotor nerve, trochlear nerve, trigeminal nerve, abducens nerve, facial nerve, vestibulocochlear (auditory) nerve, glossopharyngeal nerve, vagal nerve, accessory nerve, hypoglossal nerve, suboccipital nerve, the greater occipital nerve, the lesser occipital nerve, the greater auricular nerve, the lesser auricular nerve, the phrenic nerve, brachial plexus, radial axillary nerves, musculocutaneous nerves, radial nerves, ulnar nerves, median nerves, intercostal nerves, lumbosacral plexus, sciatic nerves, common peroneal nerve, tibial nerves, sural nerves, femoral nerves, gluteal nerves, thoracic spinal nerves, obturator nerves, digital nerves, pudendal nerves, plantar nerves, saphenous nerves, ilioinguinal nerves, gentofemoral nerves, and iliohypogastric nerves, etc.) and neurotransmitter levels can be measured in response to stimulation using various electrodes of the percutaneously implanted lead. Some embodiments of the invention may operate using any stimulation modality as long as an electrochemical sensor is positioned proximate to neural tissue to permit measurement of neurotransmitter levels.

Accordingly, the present method relates to electrode selection by determining the levels or concentration of neurotransmitters in response to stimulation. These data provide the clinician with information in which to modify the stimulation parameters to achieve efficient treatment for the patient. Diseases and/or disorders that may benefit from the described method include attention or cognitive disorders (e.g., Autistic Spectrum Disorders); mood disorder (e.g., depression, major depressive disorder, bipolar disorder, and dysthymic disorder); an anxiety disorder (e.g., panic disorder, posttraumatic stress disorder, obsessive-compulsive disorder and phobic disorder); neurodegenerative diseases (e.g., multiple sclerosis, Alzheimer's disease, amyotrophic lateral sclerosis (ALS), Parkinson's disease, Huntington's Disease, Guillain-Barre syndrome, myasthenia gravis, and chronic idiopathic demyelinating disease (CID)), movement disorders (e.g., dyskinesia, tremor, dystonia, chorea and ballism, tic syndromes, Tourette's Syndrome, myoclonus, drug-induced movement disorders, Wilson's Disease, Paroxysmal Dyskinesias, Stiff Man Syndrome and Akinetic-Ridgid Syndromes and Parkinsonism), eating disorders (e.g., overeating disorder, bulimia nervosa, and anorexia nervosa), obesity, epilepsy, tinnitus, pain, phantom pain, diabetic neuropathy.

Although representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate from this disclosure, processes, machines, manufacture, compositions of matter, means, methods, or steps, presently existing or later to be developed that perform substantially the same function or achieve substantially the same result as the corresponding embodiments described herein may be utilized without departing from the scope of the appended claims. Accordingly, the appended claims are intended to include within their scope such processes, machines, manufacture, compositions of matter, means, methods, or steps.

What is claimed:

1. A method of selecting electrodes for deep brain stimulation in a patient, wherein the electrode selection includes (i) implanting at least one electrical lead having a plurality of electrodes that are segmented about a circumference of the lead body for conducting electrical pulses by a pulse generating circuitry to a first neural tissue; and (ii) implanting at least one electrochemical sensor for sensing a level of one or several neurotransmitters in a second neural tissue; the method comprising:
controlling a pulse generator via a programming device to apply electrical pulses to the patient through the electrical lead, wherein the programming device:
i) automatically selects an electrode combination and applies stimulation in a directional manner about the circumference of the lead body to the neural tissue using the selected electrode combination;
ii) senses via the electrochemical sensor the extracellular level of one or several neurotransmitters in response to the electrical stimulation and generates data related to the neurotransmitter release for the selected electrode combination that is stored in the programmer;
wherein based upon the data, the programming device determines if another electrode combination is tested.

2. The method of claim 1 wherein the first and second neural tissue are different.

3. The method of claim 1 wherein the first and second neural tissue are the same.

4. The method of claim 1 wherein the first neural tissue is thalamus or subthalamic nucleus (STN).

5. The method of claim 4 wherein second neural tissue is the caudate-putamen or substantia nigra.

6. The method of claim 5 wherein selected electrode combinations comprise adjacent electrode pairs along the circumference of the electrical lead or along the longitudinal direction of the electrical lead.

7. A method of selecting electrodes for deep brain stimulation to apply stimulation pulses in a directional manner within a target tissue in a patient, the method comprising:
controlling a pulse generator via a programming device to apply electrical pulses to the patient through an electrical lead having a plurality of electrodes that are segmented about a circumference of a lead body, wherein the programming device:
i) automatically selects an electrode combination and applies stimulation in the directional manner about the circumference of the lead body to a first neural tissue of the patient using a selected electrode combination;
ii) sampling a neurotransmitter signal from an electrochemical sensor that is implanted in a second neural tissue in which data related to extracellular neurotransmitter release for the selected electrode combination is stored in the programming device;
wherein based upon the data, the programming device determines if another electrode combination is tested.

8. The method of claim 7 further comprising displaying the data in a graphical display that depicts data in one or more graphical controls arranged in a manner that corresponds to an electrode configuration.

* * * * *